(12) United States Patent
Roller et al.

(10) Patent No.: US 7,439,226 B2
(45) Date of Patent: Oct. 21, 2008

(54) SERINE PROTEASE INHIBITORS

(75) Inventors: Peter P. Roller, Rockville, MD (US); Peng Li, Frederick, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 10/957,266

(22) Filed: Sep. 30, 2004

(65) Prior Publication Data

US 2005/0130883 A1 Jun. 16, 2005

Related U.S. Application Data

(60) Provisional application No. 60/507,583, filed on Sep. 30, 2003.

(51) Int. Cl.
*A61K 38/00* (2006.01)
(52) U.S. Cl. ...................................................... 514/10
(58) Field of Classification Search .................... 514/10
See application file for complete search history.

(56) References Cited

U.S. PATENT DOCUMENTS

| | | | |
|---|---|---|---|
| 5,376,544 A * | 12/1994 | Lazarus et al. ............... | 435/190 |
| 5,811,515 A | 9/1998 | Grubbs et al. | |
| 6,114,308 A | 9/2000 | Claeson et al. | |
| 6,130,315 A | 10/2000 | Kolb et al. | |
| 6,218,365 B1 | 4/2001 | Adang et al. | |
| 6,346,604 B1 | 2/2002 | Wakimasu et al. | |
| 6,358,928 B1 | 3/2002 | Rasnick | |
| 6,407,059 B1 | 6/2002 | Gilon et al. | |
| 6,472,505 B1 | 10/2002 | Condon et al. | |
| 6,534,498 B1 | 3/2003 | Marquis, Jr. et al. | |
| 6,562,842 B2 | 5/2003 | Yamashita | |
| 6,583,137 B1 | 6/2003 | Marquis, Jr. et al. | |
| 6,797,504 B1 | 9/2004 | Madison et al. | |
| 2003/0050251 A1 | 3/2003 | Semple et al. | |
| 2003/0078368 A1 | 4/2003 | Roller et al. | |
| 2003/0180804 A1 | 9/2003 | Pryor et al. | |
| 2003/0181428 A1 | 9/2003 | Green et al. | |

FOREIGN PATENT DOCUMENTS

| | | | |
|---|---|---|---|
| WO | WO 00/31139 | * | 6/2000 |
| WO | WO 00/53232 | | 9/2000 |
| WO | WO 01/97794 | | 12/2001 |
| WO | WO 02/08392 | | 1/2002 |
| WO | WO 2004/058688 | | 7/2004 |

OTHER PUBLICATIONS

Jaulent, Agnes M,; McBride, Jeffrey D.; Leatherbarrow, Robin J., "Synthesis and activity of a small cyclic protease inhibitor from sunflower seeds, SFTI-1," Peptides: The Wave of the Future, Proceedings of the Second International and the Seventeenth American Peptide Symposium, San Diego, CA, United States, June 9-14, 2001, 547-548. Editor.*
Jaulent et al., "Synthesis and Activity of a Small Cyclic Protease Inhibitor from Sunflower Seeds, SFTI-1 ," Peptides: The Wave of the Future, pp. 547-548 (2001).*
Aguirre Ghiso et al., "Tumor dormancy induced by downregulation of urokinase receptor in human carcinoma involves integrin and MAPK signaling," *J. Cell. Biol.*, 147:89-104 (1999).
Greco et al., "Nonpeptide Inhibitors of Cathepsin G: Optimization of a Novel β-Ketophosphonic Acid Lead by Structure-Based Drug Design," *J. Am. Chem. Soc.*, 124:3810-3811 (2002).
Hooper et al., "Type II Transmembrane Serine Proteases," *The Journal of Biological Chemistry*, 276(2):857-860 (2001).
International Search Report from International Application No. PCT/US2004/034108.
Jaulent and Leatherbarrow, "Design, synthesis and analysis of novel bicycle and bifunctional protease inhibitors,"*Protein Engineering, Design & Selection*, 17(9):681-687 (2004).
Jaulent et al., "Synthesis and Activity of a Small Cyclic Protease Inhibitor from Sunflower Seeds, SFTI-1," *Peptides: The Wave of the Future*, pp. 547-548 (2001).
Lee et al., "Activation of Hepatocyte Growth Factor and Urokinase/Plasminogen Activator by Matriptase, an Epithelial Membrane Serine Protease," *The Journal of Biological Chemistry*, 275(47):36720-36725 (2000).
Lin et al., "Molecular cloning of cDNA for matriptase, a matrix-degrading serine protease with trypsin-like activity," *J. Biol. Chem.*, 274:18231-18236 (1999).
Lin et al., "Purification and characterization of a complex containing matriptase and a Kunitz-type serine protease inhibitor from human milk," *J. Biol. Chem.*, 274:18237-18242 (1999).
Long et al., "Synthesis and Evaluation of the Sunflower Derived Trypsin Inhibitor as a Potent Inhibitor of the Type II Transmembrane Serine Protease, Matriptase," *Bioorganic & Medicinal Chemistry Letters*, 11:2515-2519 (2001).
Luckett et al., "High-resolution structure of a potent, cyclic proteinase inhibitor from sunflower seeds," *J. Mol. Biol.*, 290:525-533 (1999).
Marx et al., "Enzymatic Cyclization of a Potent Bowman-Birk Protease Inhibitor, Sunflower Trypsin Inhibitor-1, and Solution Structure of an Acyclic Precursor Peptide," *The Journal of Biological Chemistry*, 278(24):21782-21789 (2003).
Roller et al., "Bicyclic Peptide Inhibitors of an Epithelial Cell-Derived Transmembrane Protease, Matriptase," *Peptides: The Wave of the Future*, pp. 561-562 (2001).
Written Opinion from International Application No. PCT/US2004/034108.
Zablotna et al., "Chemical synthesis and kinetic study of the smallest naturally occurring trypsin inhibitor SFTI-1 isolated from sunflower seeds and its analogues," *Peptides 2002*, pp. 780-781 (2002).

* cited by examiner

*Primary Examiner*—Cecilia Tsang
*Assistant Examiner*—Thomas S. Heard
(74) *Attorney, Agent, or Firm*—Klarquist Sparkman, LLP

(57) ABSTRACT

The present disclosure concerns peptides and peptidomimetics having inhibitory activity against serine proteases. The disclosed peptides and peptidomimetics are particularly useful as selective inhibitors of matriptase and MTSP1. Pharmaceutical compositions comprising serine protease inhibitors and methods for administering the compositions also are disclosed.

20 Claims, No Drawings

SERINE PROTEASE INHIBITORS

CROSS REFERENCE TO RELATED APPLICATION

This application claims the benefit of U.S. Provisional Application No. 60/507,583, filed Sep. 30, 2003, which is incorporated herein by reference in its entirety.

FIELD

This disclosure concerns novel serine protease inhibitors and methods for using the inhibitors to reduce tumor progression and/or metastasis. Embodiments of the inhibitors are highly effective, selective inhibitors of matriptase, which has been implicated in tissue remodeling associated with the growth of cancerous tumors and cancer metastasis.

BACKGROUND

Cancer is typically characterized by an increase in the number of abnormal, or neoplastic, cells that proliferate to form a tumor mass. Cancer cells must acquire several traits for tumor growth and progression to occur. For example, the tumor must generate new vasculature to supply blood to nourish the tumor. This process is referred to as angiogenesis. Tumor cells also must acquire the ability to spread by invading adjacent tissue and/or metastasizing to distant sites.

Angiogenesis and tumor invasion require that the normal tissue surrounding the tumor be broken down in a process referred to as tissue remodeling. Tissue remodeling is accomplished by a host of enzymes that break down the proteins in the normal tissue barriers comprising the extracellular matrix. Among the enzymes associated with degradation of the extracellular matrix and tissue remodeling are a number of proteases. The expression of some of these proteases has been correlated with tumor progression. See, Mignatti and Rifkin *Physiol. Rev.* 1993, 73, 161-165.

To date, most efforts to inhibit the tissue remodeling associated with tumor progression have focused on inhibiting one class of protease, the matrix metalloproteases (MMPs). MMPs are reported to aid tumor progression by degrading the basement membrane. Two such MMPs are the type IV collagenase and stromelysin.

Recently, it has been learned that a serine protease, matriptase, plays a role in degrading the extracellular matrix during tumor progression. PCT publication numbers WO 00/53232 and WO 01/97794 describe matriptase, methods of inhibiting carcinoma progression wherein matriptase plays a role, as well as compounds useful in those methods. PCT publication number WO 02/08392 describes matriptase-like serine proteases, methods for their identification and methods for screening agents that modulate the activity of a human matriptase-like serine protease. U.S. patent publication No. 2003/0050251, describes inhibitors of matriptase and of a related serine protease, MTSP1.

Recently, a small, cyclic 14-amino acid serine protease inhibitory peptide was isolated from sunflower seeds. The peptide, termed sunflower trypsin inhibitor (SFTI-1) exhibited subnanomolar inhibitory constants ($K_i$) against both matriptase and cathepsin G.

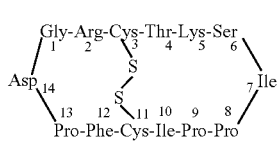

SFTI-1

STFI-1 (SEQ ID NO: 1, wherein amino acid at position 2 is arginine, amino acid at position 3 is cysteine, amino acid at position 4 is threonine, amino acid at position 5 is lysine, amino acid at position 10 is isoleucine, amino acid at position 11 is cysteine, and amino acid at position 12 is phenylalanine)

SFTI-1 also appears to be a somewhat selective inhibitor having three orders of magnitude lower inhibitory activity against elastase and thrombin than against matriptase. Moreover, SFTI-1 has no detectable effect on the activity of Factor Xa (Luckett et al. *J Mol. Biol.* 1999, 290, 525).

However, SFTI-1 has two drawbacks that prevent it from being an ideal therapeutic agent. First, SFTI-1 is believed to be degraded in vivo, thus diminishing its efficacy, and second, SFTI-1 exhibits insufficient selectivity over other serine proteases, such as trypsin and chymotrypsin.

SUMMARY OF THE DISCLOSURE

One aspect of the present disclosure includes novel compounds, compositions and methods for using such compounds and compositions to inhibit tumor progression. In one embodiment, the compounds have Formula 1, including solvates and pharmaceutically acceptable salts thereof.

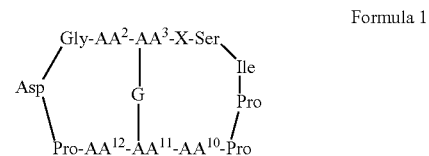

Formula 1

Formula 1 (SEQ ID NO: 1, wherein $AA^2$, $AA^3$, $AA^4$, $AA^5$, $AA^{10}$, $AA^{11}$, and $AA^{12}$ are any amino acids)

With reference to Formula 1, $AA^2$, $AA^3$, $AA^{10}$, $AA^{11}$ and $AA^{12}$ represent amino acid residues; G is an optional crosslinking group; and X is a dipeptide or dipeptide mimetic. $AA^2$, $AA^3$, $AA^{10}$, $AA^{11}$ and $AA^{12}$ can be any amino acid residue, including the residues of natural and unnatural amino acids. Typically, the selected amino acid residues are α-amino acids. $AA^2$ typically is a basic amino acid residue, $AA^{10}$ typically is a hydrophobic amino acid residue and $AA^{12}$ typically is an aromatic amino acid residue.

One embodiment of the disclosure is directed to compounds according to Formula 2.

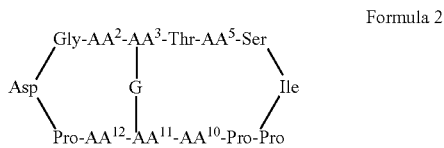

Formula 2

Formula 2 (SEQ ID NO: 1, wherein $AA^2$, $AA^3$, $AA^5$, $AA^{10}$, $AA^{11}$, and $AA^{12}$ are any amino acids and $AA^4$ is threonine)

With respect to Formula 2, variable groups $AA^2$, $AA^3$, $AA^{10}$, $AA^{11}$, $AA^{12}$ and G are defined as above with respect to Formula 1. $AA^5$ can be any amino acid residue, including natural and unnatural amino acids. Typically, $AA^5$ includes a side chain having a cationic group, such as an amine or guanidine group.

Also included in the present disclosure is a method for making novel cyclic peptides constrained by different bridging groups, which are represented, for example, by group G in Formulas 1 and 2.

According to one aspect of the disclosure, pharmaceutical compositions including an amount of one or more compound according to one or more of the formulas disclosed herein effective to decrease or inhibit the proteolytic activity of matriptase or MTSP1 are provided.

Another aspect of the disclosure includes a method for using the disclosed novel cyclic peptide derivatives to treat a pathologic condition that is ameliorated by decreasing or inhibiting serine protease activity. The method can be used to treat any pathologic condition characterized by neovascularization. Neovascularization or angiogenesis is associated with a host of different disorders, including neoplasia (such as cancer) ocular neovascular disease, hemangioma, and disorders of chronic inflammation, such as rheumatoid arthritis and Crohn's disease. Such disorders can be treated according to the presently disclosed method for inhibiting matriptase or MTSP1. In one embodiment the method includes treating a subject suspected to have metastatic cancer cells with one or more compounds according to Formula 1 to decrease or inhibit the proteolytic activity of matriptase or MTSP1, thereby retarding angiogenesis and/or tumor progression.

SEQUENCE LISTING

The amino acid sequence listed in the accompanying sequence listing are shown using standard three letter code for amino acids, as defined in 37 C.F.R. 1.822. In the accompanying sequence listing:

SEQ ID NO: 1 is the amino acid sequence for serine protease peptides, wherein Xaa can be any amino acid.

DETAILED DESCRIPTION

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

In this specification and in the claims which follow, reference will be made to a number of terms which shall be understood to have the following meanings:

"Optional" or "optionally" means that the subsequently described event or circumstance can but need not occur, and that the description includes instances where said event or circumstance occurs and instances where it does not.

Variables such as $AA^2$, $AA^3$, $AA^4$, $AA^5$ $AA^{10}$, $AA^{11}$, $AA^{12}$, G and X used throughout the disclosure are the same variables as previously defined unless stated to the contrary.

"Derivative" refers to a compound or portion of a compound that is derived from or is theoretically derivable from a parent compound.

The term "alkyl group" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 10 carbon atoms.

The term "alkenyl group" refers to a hydrocarbon group of 2 to 24 carbon atoms and structural formula containing at least one carbon-carbon double bond.

The term "alkynyl group" refers to a hydrocarbon group of 2 to 24 carbon atoms and a structural formula containing at least one carbon-carbon triple bond.

The terms "halogenated alkyl group" or "haloalkyl group" refer to an alkyl group as defined above with one or more hydrogen atoms present on these groups substituted with a halogen (F, Cl, Br, I).

The term "cycloalkyl group" refers to a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl group" is a cycloalkyl group as defined above where at least one of the carbon atoms of the ring is substituted with a heteroatom such as, but not limited to, nitrogen, oxygen, sulfur, or phosphorous.

The term "aliphatic group" is defined as including alkyl, alkenyl, alkynyl, halogenated alkyl and cycloalkyl groups as described above. A "lower aliphatic" group is a branched or unbranched aliphatic group having from 1 to 10 carbon atoms.

The term "aryl group" refers to any carbon-based aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorous. The aryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl group can be unsubstituted.

The term "aralkyl" refers to an aryl group having an alkyl group, as defined above, attached to the aryl group. An example of an aralkyl group is a benzyl group.

The term "alkyl amino" refers to alkyl groups as defined above where at least one hydrogen atom is replaced with an amino group.

The term "hydroxyl group" is represented by the formula —OH. The term "alkoxy group" is represented by the formula —OR, where R can be an alkyl group, optionally substituted with an alkenyl, alkynyl, aryl, aralkyl, cycloalkyl, halogenated alkyl, or heterocycloalkyl group as described above.

The term "hydroxyalkyl group" refers to an alkyl group that has at least one hydrogen atom substituted with a hydroxyl group. The term "alkoxyalkyl group" is defined as an alkyl group that has at least one hydrogen atom substituted with an alkoxy group described above. Where applicable, the alkyl portion of a hydroxyalkyl group or an alkoxyalkyl group can have aryl, aralkyl, halogen, hydroxy, alkoxy The term "amine group" is represented by the formula —NRR', where R and R' can be, independently, hydrogen or an alkyl, alkenyl, alkynyl, aryl, aralkyl, cycloalkyl, halogenated alkyl, or heterocycloalkyl group described above.

The term "amide group" is represented by the formula —C(O)NRR', where R and R' independently can be a hydrogen, alkyl, alkenyl, alkynyl, aryl, aralkyl, cycloalkyl, halogenated alkyl, or heterocycloalkyl group described above.

The term "amino acid" refers to both natural and unnatural amino acids in their D and L stereoisomers for chiral amino acids. Moreover, peptide compounds disclosed herein may contain asymmetric centers in addition to the chiral centers in the backbone of the peptide compound. These asymmetric centers may independently be in either the R or S configuration. It will also be apparent to those skilled in the art that certain peptide compounds disclosed herein may exhibit geometrical isomerism. Geometrical isomers include the cis and trans forms of peptide compounds of the invention having alkenyl moieties. The present compounds comprise the individual geometrical isomers and stereoisomers and mixtures thereof.

The term "amino acid" is understood to refer to both amino acids and the corresponding amino acid residues, such as are present, for example, in peptides. Natural and unnatural amino acids are well known to those of ordinary skill in the art. Common natural amino acids include, without limitation, alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr), and valine (Val). Uncommon and unnatural amino acids include, without limitation, allyl glycine (AllylGly), biphenylalanine (Bip), citrulline (Cit), 4-guanidinophenylalanine (Phe(Gu)), homoarginine (hArg), homolysine (hLys), 2-napthylalanine (2-Nal), ornithine (Orn) and pentafluorophenylalanine ($F_5$Phe).

Amino acids are typically classified in one or more categories, including polar, hydrophobic, acidic, basic and aromatic, according to their side chains. Examples of polar amino acids include those having side chain functional groups such as hydroxyl, sulfhydryl, and amide, as well as the acidic and basic amino acids. Polar amino acids include, without limitation, asparagine, cysteine, glutamine, histidine, selenocysteine, serine, threonine, tryptophan and tyrosine. Examples of hydrophobic or non-polar amino acids include those residues having nonpolar aliphatic side chains, such as, without limitation, leucine, isoleucine, valine, glycine, alanine, proline, methionine and phenylalanine. Examples of basic amino acid residues include those having a basic side chain, such as an amino or guanidino group. Basic amino acid residues include, without limitation, arginine, homolysine and lysine. Examples of acidic amino acid residues include those having an acidic side chain functional group, such as a carboxy group. Acidic amino acid residues include, without limitation aspartic acid and glutamic acid. Aromatic amino acids include those having an aromatic side chain group. Examples of aromatic amino acids include, without limitation, biphenylalanine, histidine, 2-napthylalananine, pentafluorophenylalanine, phenylalanine, tryptophan and tyrosine. It is noted that some amino acids are classified in more than one group, for example, histidine, tryptophan and tyrosine are classified as both polar and aromatic amino acids. Additional amino acids that are classified in each of the above groups are known to those of ordinary skill in the art.

"Equivalent amino acid" means an amino acid which may be substituted for another amino acid in the peptide compounds according to the invention without any appreciable loss of function. Equivalent amino acids will be recognized by those of ordinary skill in the art. Substitution of like amino acids is made on the basis of relative similarity of side chain substituents, for example regarding size, charge, hydrophilicity and hydrophobicity as described herein. The phrase "or an equivalent amino acid thereof" when used following a list of individual amino acids means an equivalent of one or more of the individual amino acids included in the list.

The term "ester" is represented by the formula —OC(O)R, where R can be an alkyl, alkenyl, alkynyl, aryl, aralkyl, cycloalkyl, halogenated alkyl, or heterocycloalkyl group described above.

The term "carbonate group" is represented by the formula —OC(O)OR, where R can be an alkyl, alkenyl, alkynyl, aryl, aralkyl, cycloalkyl, halogenated alkyl, or heterocycloalkyl group described above.

The term "carboxylic acid" is represented by the formula —C(O)OH.

The term "aldehyde" is represented by the formula —C(O)H.

The term "keto group" is represented by the formula —C(O)R, where R is an alkyl, alkenyl, alkynyl, aryl, aralkyl, cycloalkyl, halogenated alkyl, or heterocycloalkyl group described above.

The term "carbonyl group" is represented by the formula C=O.

"Cationic group" or "cationic moiety" refers to a group that is positively charged or can be positively charged. For example, a cationic group can be an amine that is capable of being protonated at a physiologically relevant pH. A second example of a cationic group is a positively charged quaternary amine.

The term "ether group" is represented by the formula R(O)R', where R and R' can be, independently, an alkyl, alkenyl, alkynyl, aryl, aralkyl, cycloalkyl, halogenated alkyl, or heterocycloalkyl group described above.

The term "halide" is defined as F, Cl, Br, or I.

"Solvate" means a physical association of a compound with one or more solvent molecules. This physical association involves varying degrees of ionic and covalent bonding, including by way of example covalent adducts and hydrogen bonded solvates. In certain instances the solvate will be capable of isolation, for example when one or more solvent molecules are incorporated in the crystal lattice of the crystalline solid. "Solvate" encompasses both solution-phase and isolable solvates. Representative solvates include ethanol associated compound, methanol associated compounds, and the like. "Hydrate" is a solvate wherein the solvent molecule(s) is/are $H_2O$.

The term "urethane" is represented by the formula —OC(O)NRR', where R and R' can be, independently, hydrogen, an alkyl, alkenyl, alkynyl, aryl, aralkyl, cycloalkyl, halogenated alkyl, or heterocycloalkyl group described above.

The groups described above can be optionally substituted with one or more substituents. The definition of any substituent or variable at a particular location in a molecule is independent of its definitions elsewhere in that molecule. Examples of suitable substituents include but are not limited to alkyl, alkenyl, alkynyl, aryl, halo, trifluoromethyl, trifluoromethoxy, hydroxy, alkoxy, oxo, alkanoyl, alkanoyloxy, aryloxy, amino, amido, alkanoylamino, aroylamino, aralkanoylamino, substituted alkanoylamino, aralkanoylamino, substituted alkanoylamino, substituted arylamino, substituted aralkanoylamino, thiol, sulfide, thiono, sulfonyl, sulfonamide, nitro, cyano, carboxy, carbamyl, substituted carbamyl and the like.

It is understood that substituents and substitution patterns of the compounds described herein can be selected by one of ordinary skill in the art to provide compounds that are chemically stable and that can be readily synthesized by techniques known in the art and further by the methods set forth in this disclosure. Reference will now be made in detail to the present preferred embodiments.

I. Serine Protease Inhibitors

One embodiment of the serine protease inhibitors disclosed herein includes compounds according to Formula 1 and their corresponding solvates and pharmaceutically acceptable salts.

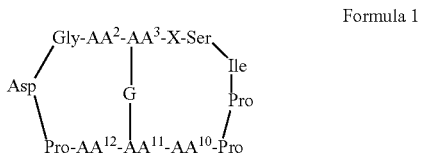

Formula 1

Formula 1(SEQ ID NO:1, wherein $AA^2$, $AA^3$, $AA^4$, $AA^5$, $AA^{10}$, $AA^{11}$, and $AA^{12}$ are any amino acids)

In Formula 1, $AA^2$, $AA^3$, $AA^{10}$, $AA^{11}$ and $AA^{12}$ represent amino acid residues; G is an optional crosslinking group; and X is a dipeptide or dipeptide mimetic. $AA^2$, $AA^3$, $AA^{10}$, $AA^{11}$ and $AA^{12}$ can be any amino acid residue, including the residues of natural and unnatural amino acids. Typically, the selected amino acid residues are α-amino acids. $AA^2$ typically is a basic amino acid residue, $AA^{10}$ typically is a hydrophobic amino acid residue and $AA^{12}$ typically is an aromatic amino acid residue.

In one embodiment of compounds according to Formula 1, $AA^2$ represents arginine, guanidinophenylalanine, homoarginine, an equivalent amino acid thereof or derivatives thereof; $AA^3$ or $AA^{11}$ independently represent cysteine, selenocysteine, serine, threonine, allyl glycine, an equivalent amino acid thereof or derivatives thereof; $AA^{10}$ represents leucine, isoleucine, valine, glycine, alanine, proline, methionine and phenylalanine, an equivalent amino acid thereof or derivatives thereof; and/or $AA^{12}$ represents biphenylalanine, histidine, 2-napthylalananine, pentafluorophenylalanine, phenylalanine, tryptophan, tyrosine, an equivalent amino acid thereof or derivatives thereof.

The amino acid residues of Formula 1 may include N-alkyl and/or N-aralkyl amide bonds. Such substitutions can be made as is known to those of ordinary skill in the art of medicinal chemistry to improve stability of a compound or to increase the affinity of a compound for the desired target.

In specific working examples, the amino acids selected for $AA^2$, $AA^3$, $AA^{10}$, $AA^{11}$ and $AA^{12}$ included allyl glycine, arginine, biphenylalanine, citrulline, glutamine, glycine, 4-guanidinophenylalanine, homoarginine, isoleucine, homolysine, lysine, 2-napthylalanine, ornithine, pentafluorophenylalanine, phenylalanine, proline, serine, and/or threonine.

Similarly, where X is a dipeptide, X includes two amino acid residues and one or both can be natural or unnatural amino acid residues. X also can be a dipeptide mimetic, such as a non-hydrolyzable dipeptide mimetic. Examples of non-hydrolyzable dipeptide mimetics include dipeptide derivatives where the otherwise hydrolyzable amide bond is replaced with a less readily hydrolyzable or non-hydrolyzable linkage. Examples of such mimetics include dipeptide isosteres, such as hydroxyethylene derivatives. Additional linkages include N-alkyl amide bonds, sulfones, phosphoramidates and phosphine oxides. Typically X includes a cationic moiety, such as a side chain amine that can be protonated at physiological pH. In particular embodiments, X includes an electrophilic moiety capable of reacting reversibly or irreversibly with an enzymatic nucleophile, such as a serine nucleophile. Examples of suitable electrophilic moieties include boronates, aldehydes, α-haloketones and the like. Examples of α-haloketones include ketones having one or more fluoride or chloride in the position α to the ketone carbonyl, such as difluoromethyl, trifluoromethyl and chloromethyl ketones.

In certain embodiments, X includes a cationic group. Thus, when X is a dipeptide, it includes a natural or non-natural basic amino acid residue. In one embodiment, X represents a dipeptide including residues selected from alanine, glycine, serine, threonine, lysine, homolysine, ornithine, arginine, aminoserine, aminopiperidinecarboxylic acid, pyrrolidinylalanine and histidine.

Examples of dipeptide residues represented by X in Formula 1 include, without limitation, threonine-containing dipeptide residues, such as threonine-lysine, lysine-threonine, threonine-homolysine, homolysine-threonine, threonine-ornithine, ornithine-threonine, threonine-arginine, arginine-threonine, threonine-aminoserine, aminoserine-threonine, threonine-aminopiperidinecarboxylic acid, aminopiperidinecarboxylic acid-threonine threonine-pyrrolidinylalanine, pyrrolidinylalanine-threonine, threonine-histidine, histidine-threonine equivalent dipeptides thereof and derivatives thereof. Other examples of cationic dipeptide residues represented by X include, without limitation, alanine, glycine and serine-containing dipeptide residues, such as alanine-lysine, lysine-alanine, alanine-homolysine, alanine-ornithine, ornithine-alanine, alanine-arginine, alanine-aminoserine, alanine-aminopiperidinecarboxylic acid, alanine-pyrrolidinylalanine, alanine-histidine, glycine-lysine, glycine-homolysine, homolysine-glycine, glycine-ornithine, glycine-arginine, glycine-aminoserine, glycine-aminopiperidinecarboxylic acid, glycine-pyrrolidinylalanine, glycine-histidine, histidine-glycine, serine-lysine, serine-homolysine, serine-ornithine, serine-arginine, arginine-serine, serine-aminoserine, serine-aminopiperidinecarboxylic acid, serine-pyrrolidinylalanine, pyrrolidinylalanine-serine, serine-histidine, equivalent dipeptides thereof and derivatives thereof.

With continued reference to Formula 1, G is an optional crosslinking group, for example, in one embodiment, Formula 1 represents a bicyclic compound. Examples of crosslinking groups include amides, esters, thioesters, ethers, sulfides, disulfides, diselenides, aromatic and aliphatic groups, such as optionally substituted lower aliphatic carbon chains. G can be optionally substituted with one or more moieties selected from aryl, heteroaryl, aralkyl, alkyl, haloalkyl, alkyl amino, hydroxyl, hydroxyalkyl, halogen and alkoxyalkyl groups.

In one embodiment G is selected such that it is not degraded under physiological conditions and in additional embodiments G is selected such that it rigidifies the peptide or peptide mimetic, for example by stabilizing a conformation recognized by a target enzyme. In such embodiments G typically is an optionally substituted linker having a length (between the alpha carbons of $AA^3$ and $AA^{11}$) of from about 2 angstroms to about 50 angstroms, such as from about 3 angstroms to about 20 angstroms or from about 3 to about 12 angstroms. Wherein, G is an optionally substituted aliphatic chain, optionally interrupted with one or more heteroatoms, the chain is typically from 1 to about 10 atoms in length, such as from 2 to 6 atoms in length.

In certain embodiments, the crosslinking group is conveniently formed from the side chain of $AA^3$, $AA^{11}$, or both. The G linking group can be installed in a ring closing reaction or can be installed prior to ring closing. The crosslinking group can be selected so that it is stable to reduction in vivo. For example, ethers, sulfides and aliphatic groups all provide linkages stable to in vivo reduction. Working examples included compounds according to Formula 1 having G be a cystine bridge, wherein $AA^3\text{-}G\text{-}AA^{11}$ represents cysteine residues linked through their side chains by a disulfide bond (cysteine-S—S-cysteine), an alkyl bridge or an alkenyl bridge.

One embodiment of the disclosure is directed to compounds according to Formula 2.

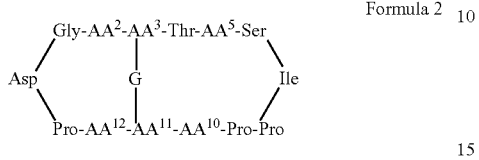

Formula 2

With respect to Formula 2, variable groups $AA^2$, $AA^3$, $AA^{10}$, $AA^{11}$, $AA^{12}$ and G are defined as above with respect to Formula 1. $AA^5$ can be any amino acid residue, including natural and unnatural amino acids. In embodiments of compounds according Formula 2 $AA^5$ represents arginine, homolysine, lysine, an equivalent amino acid thereof or derivatives thereof.

Typically, $AA^5$ includes a side chain having a cationic group, such as an amine or guanidine group. Cationic group optionally can be alkylated to yield a side chain substituted with an alkyl, aralkyl and/or haloalkyl group. Suitable amino acids for incorporation as $AA^5$ include, without limitation, arginine, aminopiperidinecarboxylic acid, diaminobutanoic acid, histidine, lysine, homolysine, ornithine, pyrrolidinyl alanine and the like. In working examples, amino acid residues used as $AA^5$ included arginine, lysine, homolysine and ornithine.

In another embodiment, inhibitors have an amide, ester, thioester, ether or sulfide bridge according to Formula 3. Ether and thioether bridging groups are particularly preferred due to their relative stability.

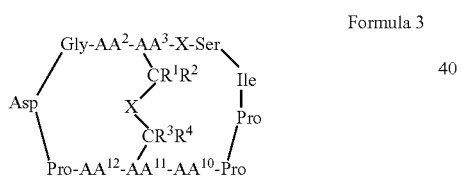

Formula 3

Formula 3 (SEQ ID NO: 1, wherein $AA^2$, $AA^3$, $AA^4$, $AA^5$, $AA^{10}$, $AA^{11}$, and $AA^{12}$ are any amino acids)

With respect to Formula 3 X is O, S, $NR^5$, or a lower aliphatic group; $R^1$, $R^2$, $R^3$, $R^4$ and $R^5$ independently are hydrogen, lower alkyl, haloalkyl and/or aralkyl and one of the groups $CR^1R^2$ and $CR^3R^4$ can represent $C=O$.

Thus, in one embodiment, $AA^3\text{-}G\text{-}AA^{11}$ represents a moiety, such as

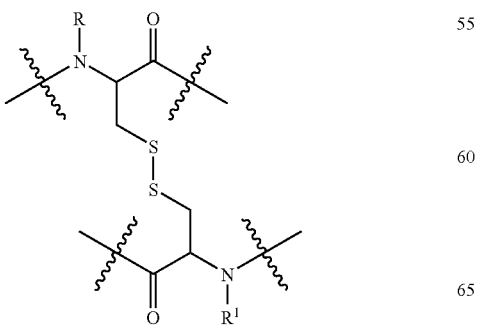

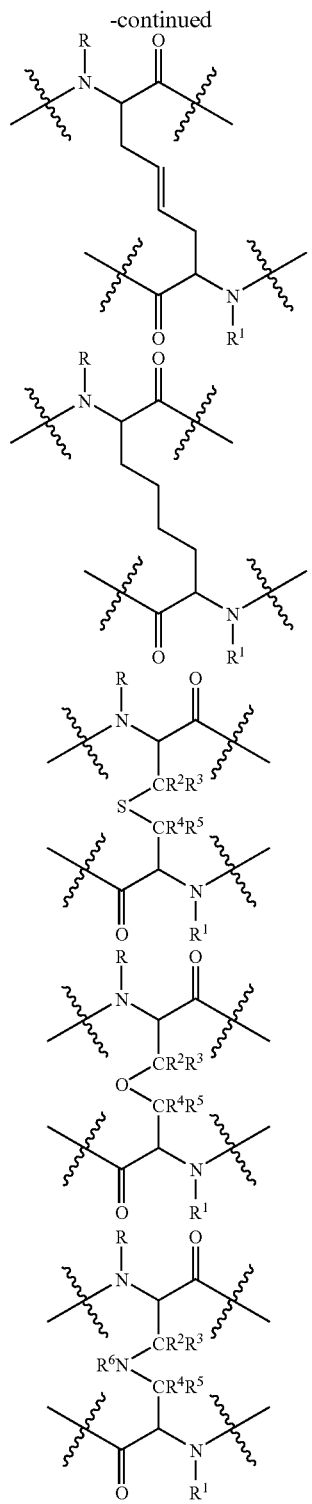

wherein $R^1$, $R^2$, $R^3$, $R^4$ and $R^5$ independently are selected from the groups recited above.

The disclosed compounds also encompass salts including, if several salt-forming groups are present, mixed salts and/or internal salts. The salts are generally pharmaceutically-acceptable salts that are non-toxic. Examples of salt-forming acidic groups include, but are not limited to, a carboxyl group, a phosphonic acid group or a boronic acid group, that can form salts with suitable bases. These salts can include, for example, nontoxic metal cations which are derived from metals of groups IA, IB, IIA and IIB of the periodic table of the elements. In one embodiment, alkali metal cations such as lithium, sodium or potassium ions, or alkaline earth metal cations such as magnesium or calcium ions can be used. The salt can also be a zinc or an ammonium cation. The salt can also be formed with suitable organic amines, such as unsubstituted or hydroxyl-substituted mono-, di- or tri-alkylamines, in particular mono-, di- or tri-alkylamines, or with quaternary ammonium compounds, for example with N-methyl-N-ethylamine, diethylamine, triethylamine, mono-, bis- or tris-(2-hydroxy-lower alkyl)amines, such as mono-, bis- or tris-(2-hydroxyethyl)amine, 2-hydroxy-tert-butylamine or tris(hydroxymethyl)methylamine, N,N-di-lower alkyl-N-(hydroxy-lower alkyl)amines, such as N,N-dimethyl-N-(2-hydroxyethyl)amine or tri-(2-hydroxyethyl)amine, or N-methyl-D-glucamine, or quaternary ammonium compounds such as tetrabutylammonium salts.

Particular compounds possess at least one basic group that can form acid-base salts with inorganic acids. Examples of basic groups include, but are not limited to, an amino group or imino group. Examples of inorganic acids that can form salts with such basic groups include, but are not limited to, mineral acids such as hydrochloric acid, hydrobromic acid, sulfuric acid or phosphoric acid. Basic groups also can form salts with organic carboxylic acids, sulfonic acids, sulfo acids or phospho acids or N-substituted sulfamic acid, for example acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, and, in addition, with amino acids, for example with α-amino acids, and also with methanesulfonic acid, ethanesulfonic acid, 2-hydroxymethanesulfonic acid, ethane-1,2-disulfonic acid, benzenedisulfonic acid, 4-methylbenzenesulfonic acid, naphthalene-2-sulfonic acid, 2- or 3-phosphoglycerate, glucose-6-phosphate or N-cyclohexylsulfamic acid (with formation of the cyclamates) or with other acidic organic compounds, such as ascorbic acid.

II. Selection of Preferred Compounds

Preferred compounds for treating a subject are typically selected for their potency and selectivity in inhibiting the serine protease activity of matriptase or MTSP1. As described under General Methods, below, and as is generally known, efficacy of particular inhibitors against a target protease is determined in vitro by combining the target protease with a substrate both in the absence of the inhibitor and in the presence of several different concentrations of inhibitor. Typically, the efficacy of the inhibitor is measured in terms of a $K_i$ value. Within a series of compounds assayed, greater inhibitory efficacy is indicated by lower $K_i$ values. Preferred compounds for use in the disclosed methods have low $K_i$ values, for example, such compounds typically have a $K_i$ value of less than about 10 micromolar, and more typically less than 1 micromolar against matriptase, MTSP1, or both. However, preferred compounds need not have a $K_i$ value lower than that of SFTI-1 to be a preferred inhibitor. For example, particularly preferred inhibitors have $K_i$ values of less than about 500 nanomolar, and working examples included inhibitors with $K_i$ values of less than 50 nanomolar against matriptase.

By way of example, several disclosed inhibitors having Formula 1 have been evaluated for matriptase inhibition. The results of these studies are recorded in Table 1. With reference to Table 1 and Formula 1, the observed $K_i$ of SFTI-1 against matriptase (0.92 nanomolar) was set to 1 for ease of comparison with the other inhibitors. With the exception of SFTI-4, each inhibitor described in Table 1 has a $K_i$ of less than 1 micromolar against matriptase.

In one aspect, preferred inhibitors effectively inhibit matriptase, MTSP1, or both without appreciably inhibiting the activity of other physiologically important serine proteases, particularly thrombin. Typically, preferred inhibitors are characterized by having a selectivity (as demonstrated, for example, by $K_i$ values) of at least about two-fold for matriptase, MTSP1, or both than for thrombin. More typically, preferred inhibitors have a selectivity for matriptase, MTSP1, or both over thrombin of greater than an order of magnitude.

TABLE 1

Inhibitor Formula (Formula 1)
(SEQ ID NO: 1)

$$\begin{array}{c} Gly-AA^2-AA^3-X-Ser \\ Asp \diagup \quad | \quad | \quad \diagdown Ile \\ \quad \quad G \quad | \\ \quad \quad | \quad Pro \\ Pro-AA^{12}-AA^{11}-AA^{10}-Pro \end{array}$$

| Inhibitor Code | AA² | X | AA³-G-AA¹¹ | AA¹⁰ | AA¹² | Relative Matriptase Inhibitory Activity [Ki (nm)] |
|---|---|---|---|---|---|---|
| SFTI-1 | Arg | Thr-Lys | Cystine (cysteine-S-S-cysteine) | Ile | Phe | 1 |
| SFTI-3 | Arg | Thr-Arg | Cystine | Ile | Phe | 47.5 |
| SFTI-4 | Arg | Thr-Orn | Cystine | Ile | Phe | >2500 |
| SFTI-5 | Phe(Gu) | Thr-Lys | Cystine | Ile | Phe | 900 |
| SFTI-6 | Cit | Thr-Lys | Cystine | Ile | Phe | 225 |
| SFTI-7 | Arg | Thr-hLys | Cystine | Ile | Phe | 280 |
| SFTI-8 | Arg | Thr-Lys | Ser, Ser monocyclic peptide | Ile | Phe | 1070 |

TABLE 1-continued

Inhibitor Formula (Formula 1) (SEQ ID NO: 1)

```
        Gly—AA²—AA³—X—Ser
       /         |      \Ile
    Asp          G        |
       \         |        Pro
        Pro—AA¹²—AA¹¹—AA¹⁰—Pro
```

| Inhibitor Code | AA² | X | AA³-G-AA¹¹ | AA¹⁰ | AA¹² | Relative Matriptase Inhibitory Activity [Ki (nm)] |
|---|---|---|---|---|---|---|
| SFTI-9 | Arg | Thr-Lys | AllylGly-AllylGly alkene bridge | Ile | Phe | 25 |
| SFTI-10 | Arg | Thr-Lys | Cystine | Gln | Phe | 23.3 |
| SFTI-11 | Arg | Thr-Lys | Cystine | Ile | 2-Nal | 4.5 |
| SFTI-12 | Arg | Thr-Lys | Cystine | Ile | Bip | 10 |
| SFTI-13 | Arg | Thr-Lys | Cystine | Ile | F₅Phe | 8.9 |
| SFTI-14 | hArg | Thr-Lys | Cystine | Ile | Phe | 8.57 |
| SFTI-15 | Arg | Thr-Lys | AllylGly-AllylGly alkyl bridge | Ile | Phe | 2.5-fold less potent than SFTI-1 at 40 µM |

III. Pharmaceutical Compositions

Another aspect of the disclosure includes pharmaceutical compositions prepared for administration to a subject and which include a therapeutically effective amount of one or more of the currently disclosed compounds. The therapeutically effective amount of a disclosed compound will depend on the route of administration, the type of mammal that is the subject and the physical characteristics of the subject being treated. Specific factors that can be taken into account include disease severity and stage, weight, diet and concurrent medications. The relationship of these factors to determining a therapeutically effective amount of the disclosed compounds is understood by those of ordinary skill in the art.

Any of the peptides and peptidomimetics described herein can be combined with a pharmaceutically acceptable carrier to form a pharmaceutical composition. Pharmaceutical carriers are known to those skilled in the art. These most typically would be standard carriers for administration of compositions to humans, including solutions such as sterile water, saline, and buffered solutions at physiological pH. The compositions could also be administered intramuscularly, subcutaneously, or in an aerosol form. Other compounds will be administered according to standard procedures used by those skilled in the art.

Molecules intended for pharmaceutical delivery can be formulated in a pharmaceutical composition. Pharmaceutical compositions can include carriers, thickeners, diluents, buffers, preservatives, surface active agents and the like in addition to the molecule of choice. Pharmaceutical compositions can also include one or more additional active ingredients such as antimicrobial agents, anti-inflammatory agents, anesthetics, and the like. Pharmaceutical formulations can include additional components, such as carriers. The pharmaceutically acceptable carriers useful for these formulations are conventional. *Remington's Pharmaceutical Sciences*, by E. W. Martin, Mack Publishing Co., Easton, Pa., 15th Edition (1975), describes compositions and formulations suitable for pharmaceutical delivery of the compounds herein disclosed.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

In some embodiments, sustained intra-tumoral (or near-tumoral) release of the pharmaceutical preparation that comprises an effective amount of a disclosed protease inhibitor can be beneficial. Slow-release formulations are known to those of ordinary skill in the art. By way of example, polymers such as bis(p-carboxyphenoxy)propane-sebacic-acid or lecithin suspensions can be used to provide sustained intra-tumoral release.

It is specifically contemplated in some embodiments that inhibitor delivery is via an injected and/or implanted drug depot, for instance comprising multi-vesicular liposomes such as in DepoFoam (SkyePharma, Inc, San Diego, Calif.) (see, for instance, Chamberlain et al. *Arch. Neuro.* 1993, 50, 261-264; Katri et al. *J. Pharm. Sci.* 1998, 87, 1341-1346; Ye et al., *J. Control Release* 2000, 64, 155-166; and Howell, *Cancer J.* 2001, 7, 219-227).

IV. Methods for Using the Disclosed Compounds

The disclosed compounds can be used to inhibit matriptase, MTSP1, or both, in vitro and in vivo and thus can be used in the prevention or treatment of conditions characterized by abnormal or pathological serine protease activity. For example, the compounds are useful for prevention or treatment of conditions characterized by the pathological degradation of the extracellular matrix, such as conditions characterized by neovascularization or angiogenesis, including cancerous conditions, particularly metastatic cancerous conditions wherein matriptase is implicated. The disclosed compounds can be used to decrease the degradation of the cellular matrix and thereby reduce concomitant tumor progression and metastasis. Conditions characterized by abnormal or pathological serine protease activity that can be treated according to the disclosed method include those characterized by abnormal cell growth and/or differentiation, such as cancers and other neoplastic conditions. Typical examples of cancers that may be treated according to the disclosed inhibitors and method include colon, pancreatic, prostate, head and neck, gastric, renal, and brain cancers.

The disclosed compounds also can be used to treat non-cancerous conditions involving abnormal neovascularization or angiogenesis. Examples of such conditions include, without limitation, ocular neovascular disease, hemangioma, and disorders of chronic inflammation, such as rheumatoid arthritis and Crohn's disease. Such disorders can be treated according to the presently disclosed method for inhibiting matriptase or MTSP1.

The method includes administering at least one disclosed novel matriptase inhibitor to a subject in an amount sufficient to elicit a therapeutic response, for example, the inhibition of carcinoma progression. The subject typically will be a mammal, such as a rodent or primate, and specifically a mouse or human.

The inhibitor or inhibitors may be administered by any pharmaceutically acceptable means, by either systemic or local administration. Modes of administration include oral, dermal, such as using a transdermal patch, inhalation, infusion, intranasal, rectal, vaginal, topical parenteral, including intraperitoneal, intravenous, intramuscular and subcutaneous injection. Pharmaceutically acceptable formulations and compositions are described above.

Typically, oral administration or administration via injection is preferred. The inhibitors may be provided in a single dosage or chronically, dependent upon the particular disease, condition of patient, toxicity of compound and other factors as will be recognized by a person of ordinary skill in the art.

The therapeutically effective amount of the compound or compounds administered can vary depending upon the desired effects and the factors noted above. In particular examples dosages are administered that achieve target tissue concentrations that have been found to be effective in vitro. Typically, dosages will be between about 0.01 mg/kg and 100 mg/kg of the subject's body weight, and more typically between about 0.05 mg/kg and 10 mg/kg, such as from about 0.2 to about 5 mg/kg of the subject's body weight.

The disclosed compounds may be used alone, in combination with other matriptase inhibitors. Moreover, the disclosed inhibitors may be used with other types of treatments, such as cancer treatments. For example the disclosed inhibitors may be used with other chemotherapies, such as tamoxifen, taxol, methotrexate, and biologicals, such as antibodies, growth factors and/or lymphokines. Additionally, the disclosed inhibitors can be used in combination with radiation therapy, surgery, or other modalities of cancer therapy.

Animal models can be used to assess the ability of the disclosed compounds to inhibit or retard tumor progression. For example, these models include transgenic animals, such as transgenic rodents, or host animals transplanted with tumor cells originally derived from mice, rats or humans. Appropriate animal models can be selected based upon criteria known to those of ordinary skill in the art. For example, one criterion is the expression of matriptase or MTSP1 by the particular tumor in the model. Examples of cell lines that meet this criterion include LnCap and PC-3 cell lines derived from human prostate tissue. Primary breast carcinoma cells and ovarian tumor cells are further examples of useful cell lines for evaluating matriptase inhibitors. These cell lines can be used to evaluate matriptase inhibitors both in vitro and in vivo. Another criterion may be that the tumor is derived from a tissue that normally expresses high levels of matriptase or MTSP1. Examples of cancers that meet this criterion include ovarian, colon and breast cancers. Another model for evaluating the disclosed inhibitors is the chick embryo chorioallantoic membrane model, which can be used to measure the ability of compounds to inhibit angiogenesis. See, Ghiso et al. *J. Cell. Biol.* 1999, 147, 89-104, which is incorporated herein by reference.

The disclosed compounds also are useful, for example, in in vitro assays, such as assays directed to identifying new inhibitors of matriptase and/or MTSP-1. The compounds also can be used to monitor matriptase or MTSP1 activity in tissue samples, such as in a clinical situation from biopsy. Another in vitro application of the disclosed compounds is affinity chromatography. Because the presently disclosed compounds bind to matriptase with high affinity, the compounds can be used to purify matriptase, or remove matriptase from a sample. To use the compounds, they typically are attached to a solid support as is known to those of ordinary skill in the art. The compounds can be attached directly or via a linker molecule. Exemplary affinity chromatography techniques suitable for use with the disclosed compounds are disclosed in Current Protocols in Protein Science, John Wiley & Sons (J. E. Coligan et al., Eds.).

V. Synthesis

The synthesis of the novel, presently disclosed compounds can be accomplished using standard chemical reactions known to be useful for preparing a variety of analogous compounds. Indeed, exemplary techniques known to those of ordinary skill in the art of peptide and peptidomimetic synthesis are taught by Bodanszky, M. and Bodanszky, A.; *The Practice of Peptide Synthesis*; Springer Verlag, N.Y., 1994; and by Jones, J.; *Amino Acid and Peptide Synthesis;* 2nd ed.; Oxford University Press, 2002, both of which are incorporated herein by reference. The Bodanszky and Jones references detail the parameters and techniques for activating and coupling amino acids and amino acid derivatives. Moreover, the references teach how to select, use and remove various useful protecting groups.

The bridging groups installed by the method are generally stable to in vivo reduction. Bridging groups can be installed as is known to those of ordinary skill in the art of organic synthesis. For example, thioether bridged compounds can be prepared by reacting a precursor having a disulfide bond between $AA^{11}$ and $AA^{12}$ with a sulfur extrusion reagent, such as is disclosed by Harpp et al. *J. Org. Chem.* 1971, 36, 73 and Krajewski et al. *Bioorg. Med Chem. Lett.* 2003, 13, 3203. Both the Harpp and Krajewski disclosures are incorporated herein by reference. Alternatively, the thioether compounds can be synthesized from the corresponding disulfides via a base catalyzed elimination/Michael addition protocol, as disclosed by Galante et al. *Letters in Peptide Science* 2002, 8, 247. The Galante disclosure is incorporated herein by reference.

Amide-bridged cyclic peptide compounds are prepared by formation of an amide bond between the side-chain carboxyl group of an acidic amino acid residue and the side-chain amino group of a basic amino acid residue in the presence of a coupling agent as described herein. Examples of suitable acidic amino acid residues include aspartic acid and glutamic acid, and examples of suitable basic amino acid residues include histidine, lysine, ornithine and the like.

Ester-bridged cyclic peptide compounds are prepared by formation of an ester bond between the side-chain carboxyl group of an acidic amino acid residue and the side chain hydroxyl group of a hydroxyl or sulfhydryl-containing amino acid residue. Representative acidic amino acid residues for forming ester-bridged compounds include aspartic acid and glutamic acid. Examples of suitable amino acid residues containing a side-chain hydroxyl or sulfhydryl group include serine, threonine, tyrosine, cysteine and the like. Formation of the ester bond is accomplished using the coupling methods and reagents described herein for the formation of amide bonds.

In one embodiment of the method, a peptide containing two unsaturated aliphatic groups is subjected to alkene or enyne metathesis conditions, thereby forming a cyclic or bicyclic peptide. In this embodiment, alkene-containing and/or alkyne-containing amino acids or amino acid derivatives are used as cyclization precursors. In the case of alkene metathesis precursors, two alkene-containing amino acid residues are incorporated, for example, with reference to Formula 1, as $AA^{11}$ and $AA^{12}$. The products of alkene metathesis performed using such precursors have a structure according to Formula 4.

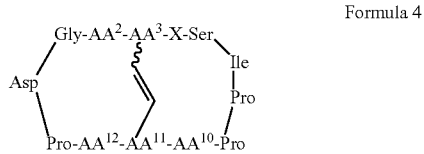

Formula 4

Formula 4 (SEQ ID NO: 1, wherein $AA^2$, $AA^3$, $AA^4$, $AA^5$, $AA^{10}$, $AA^{11}$, and $AA^{12}$ are any amino acids)

In the case of enyne metathesis, an alkene-containing and an alkyne-containing amino acid or amino acid derivative are used to install the bridging group. Useful alkene-containing amino acids include allyl glycine; useful alkyne-containing amino acids include propargyl glycine. Both alkene and enyne metathesis reactions result in an alkene-containing bridge, which optionally can be reduced to provide an alkyl bridging group.

The details of the preparation of several exemplary embodiments of the disclosed protease inhibitors are described below.

EXAMPLES

The foregoing disclosure is further explained by the following non-limiting examples.

General Methods $N_\alpha$-Fmoc-protected amino acids were purchased from Perkin-Elmer/Applied Biosystems Division (Foster City, Calif.). Fmoc-L-2-Nal-OH, Fmoc-Gly-Rink resin and Fmoc-L-Bip-OH were purchased from Advanced ChemTech (Louisville, Ky.). Fmoc-L-pentafluorophenylalanine-OH was purchased from SyntheTech, Inc (Albany, Oreg.). Fmoc-L-allylGly-cine-OH was purchased from Peptech Corporation (Burlington, Mass.). Fmoc-L-Orn(Boc)-OH was purchased from Bachem (Torrance, Calif.). Trifluoroacetic acid (TFA), triethylsilane (TES) and O-(7-Azabenzotriazol-1-yl)-N,N,N',N'-tetramethyluronium hexafluorophosphate (HATU) were purchased from Aldrich Chemical Company, Inc. (Milwaukee, Wis.). 1-Hydroxy-7-azabenzotriazole (HOAt) was purchased from Millipore (Bedford, Mass.). Benzylidene-bis(tricyclo-hexylphosphine-dichlororuthenium was purchased from Fluka (Milwaukee, Wis.). Mass spectra were recorded on Kompact Axima-CFR MALDI and VG Analytical 7070E-HF FAB (unit resolution, glycerol matrix) mass spectrometers. Linear peptides were synthesized on an Applied Biosystems 433A peptide synthesizer. Peptides were purified and analyzed by reversed-phase HPLC using a Beckman system.

HPLC conditions I: Vydac C4 column (22×250 mm); solvent system, A, was 0.05% TFA in water; B, 0.05% TFA in 90% acetonitrile in water; gradient, 10%-80% B over 30 minutes; flow rate, 10.0 mL/minute; UV detector 225 nm. HPLC conditions II: Vydac C18 column (22×250 mm); solvent system, A, 0.05% TFA in water; B, 0.05% TFA in 90% acetonitrile in water; gradient, 0%-50% B over 30 minutes; flow rate, 15.0 mL/minute; UV detector 225 nm. HPLC conditions III: Vydac C8 column (22×250 mm); solvent system, A, 0.05% TFA in water; B, 0.05% TFA in 90% acetonitrile in water; gradient, 10%-80% B over 30 minutes; flow rate, 10.0 mL/minute; UV detector 225 nm.

The 70-kDa activated matriptase was isolated as described by Lin et al. *J. Biol. Chem.* 1999, 274, 18231; Kim et al. *Immunogenetics* 1999, 49, 420; and Lin et al. *J. Biol. Chem.* 1999, 274, 18237. Urokinase-type plasminogen activator (uPA) was purified by aminobenzamidine-Sepharose 6B (Amersham Pharmacia, Piscataway, N.J.) from a partially purified uPA from human urine. Bovine β-trypsin, bovine thrombin, Bowman-Birk inhibitor (BBI), and the fluorescent substrates were purchased from Sigma (Sigma Chemical Co., St. Louis, Mo.).

Inhibitory activity of SFTI-1 and the disclosed inhibitors was measured at room temperature in a reaction buffer of 100 mM Tris-HCl (pH 8.5) containing 100 mg/mL of bovine serum albumin, using the fluorescent substrate peptides. To a cuvette containing 170 µL of reaction buffer was added 10 µL of enzyme solution and 10 µL of inhibitor solution. After preincubation, 10 µL of substrate solution was added and the cuvette content mixed thoroughly. The residual enzyme activity was determined by following the change of fluorescence released by hydrolysis of the substrates, using a fluorescent spectrophotometer (Hitachi F4500) using an excitation wavelength of 360 nm and monitoring emission at 480 nm. Fluorescent peptide N-t-Boc-Gln-Ala-Arg-AMC was used as a substrate for matriptase and trypsin, peptide N-t-Boc-Leu-Gly-Arg-AMC was used as a substrate for uPA, and peptide N-t-Boc Leu-Arg-Arg-AMC was used as a substrate for thrombin. The specificity of the disclosed inhibitors for matriptase versus other proteases can be determined as described by Semple, et al. in U.S. patent application Ser. No. 10/092,004, filed Mar. 13, 2003, and which is incorporated herein by reference. Hydrolysis rates were recorded in the presence of different concentrations of inhibitors and the $K_i$ values were determined by Dixon plots from two sets of data with different concentrations of substrate. Table 2 illustrates the relative activity of SFTI-1 against different serine proteases.

TABLE 2

| Protease | $K_i$ of SFTI-1 (nM) |
| --- | --- |
| Matriptase | 0.92 |
| Trypsin | 1.06 |
| Thrombin | 5,050 |
| uPA | 500,000 |

Example 1

This example describes the synthesis of SFTI-3.

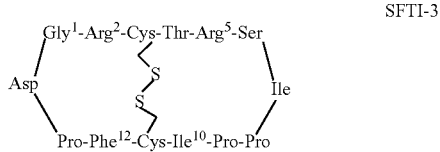

SFTI-3

SFTI-3 (SEQ ID NO: 1, wherein $AA^2$ is arginine, $AA^3$ is cysteine, $AA^4$ is threonine, $AA^5$ is arginine, $AA^{10}$ isoleucine, $AA^{11}$ is cysteine, and $AA^{12}$ is phenylalanine)

Using an ABI 433A peptide synthesizer and FastMoc chemistry (Field et al. *Pep. Res.* 1991, 4, 95), the linear side-chain protected peptide RCTRSIPPICFPDG was synthesized on the Fmoc-Gly-Rink acid resin (0.25 g, 0.1 mmol, 0.4 mmol/g). HBTU was used as a coupling reagent, and HOBt was added to promote the coupling reactions. The $N^\alpha$-Fmoc group of the resin-bound protected peptide was removed with 20% piperidine/DMF. After cycles of deprotection and coupling, the $NH_2$—R(Pmc)C(Trt)T(Bu$^t$)R(Pmc)S(Bu$^t$)IPPIC(Trt)FPD(Bu$^t$)G-Rink resin was obtained. This resin-bound peptide was then cleaved from the rink resin using 2% TFA/$CH_2Cl_2$ (1 min, repeated 5 times). The cleavage solution was collected by filtration and neutralized with 10% N-methylmorpholine (NMM)/$CH_2Cl_2$ (v/v) in an ice bath. The combined neutralized solution was evaporated to dryness in vacuo.

For backbone cyclization, the crude sidechain protected peptide $NH_2$—R(Pmc)C(Trt)T(Bu$^t$)R(Pmc)S(Bu$^t$)IPPIC(Trt)FPD(Bu$^t$)G-OH was dissolved in anhydrous $CH_2Cl_2$ (120 mL), and then HATU (190 mg, 0.5 mmol) and a solution of HOAt (68 mg, 0.5 mmol) and DEEA (174 μL, 1 mmol) in $CH_2Cl_2$ (5 mL) were added. The reaction mixture was stirred at room temperature overnight, then evaporated in vacuo. The residue was treated with 95% TFA containing 2.5% each of TES and water to deprotect the sidechains. Subsequently, for oxidation to the corresponding disulfide, the crude head-to-tail cyclized peptide was dissolved in 200 mL water and adjusted to pH=7.1 with NMM. The disulfide cyclization occurred spontaneously under neutral to weak basic conditions while bubbling the solution with oxygen at room temperature for 24 h. The reaction mixture was then acidified with 30% acetic acid to pH=3~4 and lyophilized. The crude product was purified by RP-HPLC, ((Retention time=18.0 minutes; gradient 10-80% B over 30 min); FAB-MS $(M+H)^+$ 1542.7 (Calcd.$_{ave}$ 1541.8)).

Example 2

This example describes the purification and characterization of SFTI-4

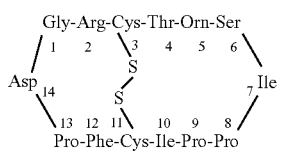

SFTI-4

SFTI-4 (SEQ ID NO: 1, wherein amino acid at position 2 is arginine, amino acid at position 3 is cysteine, amino acid at position 4 is threonine, amino acid at position 5 is ornithine, amino acid at position 10 is isoleucine, amino acid at position 11 is cysteine, and amino acid at position 12 is phenylalanine)

With reference to SFTI-4, an ornithine residue (Orn) is incorporated at position 5 in place of the lysine found in SFTI-1. The synthesis proceeded by the general method described for the synthesis of SFTI-3 in example 1. Direct HPLC purification of the crude SFTI-4 afforded by TFA mediated deprotection was performed using HPLC Conditions "I" described above ((Retention time=17.5 minutes); FAB-MS $(M+H)^+$ 1501.1 (Calcd.$_{ave}$ 1527.8)).

Example 3

This example describes the purification and characterization of SFTI-5.

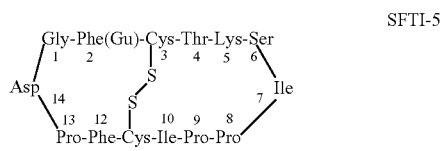

SFTI-5

SFTI-5 (SEQ ID NO: 1, wherein amino acid at position 2 is phenylalanine (Gu), amino acid at position 3 is cysteine, amino acid at position 4 is threonine, amino acid at position 5 is lysine, amino acid at position 10 is isoleucine, amino acid at position 11 is cysteine, and amino acid at position 12 is phenylalanine)

With reference to SFTI-5, a 4-phenylguanidinium residue [Phe(Gu)] is incorporated at position 2 in place of the arginine found in SFTI-1. The synthesis proceeded by the general method described for the synthesis of SFTI-3 in example 1. Direct HPLC purification of the crude SFTI-5 afforded by TFA mediated deprotection was performed using HPLC Conditions "I" described above ((Retention time=18.2 minutes); FAB-MS $(M+H)^+$ 1563.1 (Calcd.$_{ave}$ 1561.8)).

Example 4

This example describes the purification and characterization of SFTI-6.

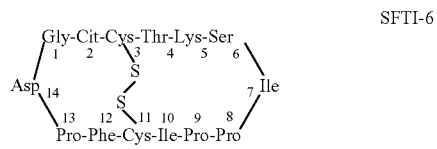

SFTI-6

SFTI-6 (SEQ ID NO: 1, wherein amino acid at position 2 is citrulline, amino acid at position 3 is cysteine, amino acid at position 4 is threonine, amino acid at position 5 is lysine, amino acid at position 10 is isoleucine, amino acid at position 11 is cysteine, and amino acid at position 12 is phenylalanine)

With reference to SFTI-6, a citrulline residue (Cit) is incorporated at position 2 in place of the arginine found in SFTI-1. The synthesis proceeded by the general method described for the synthesis of SFTI-3 in example 1. Direct HPLC purification of the crude SFTI-6 afforded by TFA mediated deprotection was performed using HPLC Conditions "I" described above ((Retention time=18.9 minutes; FAB-MS $(M+H)^+$ 1516.0 (Calcd.$_{ave}$ 1514.8)).

Example 5

This example describes the purification and characterization of SFTI-7.

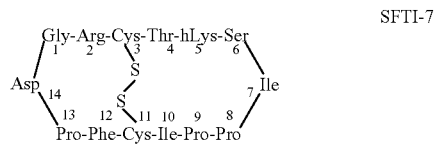

SFTI-7

SFTI-7 (SEQ ID NO: 1, wherein amino acid at position 2 is arginine, amino acid at position 3 is cysteine, amino acid at position 4 is threonine, amino acid at position 5 is (h)lysine, amino acid at position 10 is isoleucine, amino acid at position 11 is cysteine, and amino acid at position 12 is phenylalanine)

With reference to SFTI-7, a homolysine residue (hLys) is incorporated at position 5 in place of the lysine found in SFTI-1. The synthesis proceeded by the general method described for the synthesis of SFTI-3 in example 1. Direct HPLC purification of the crude SFTI-7 afforded by TFA mediated deprotection was performed using conditions 'I' described above ((Retention time=17.9 minutes); FAB-MS (M+H)$^+$1528.1 (Calcd.$_{ave}$ 1527.8)).

Example 6

This example describes the synthesis of SFTI-8.

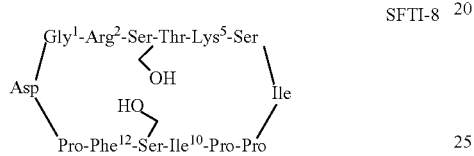

SFTI-8

SFTI-8 (SEQ ID NO: 1, wherein amino acid at position 2 is arginine, amino acid at position 3 is serine, amino acid at position 4 is threonine, amino acid at position 5 is lysine, amino acid at position 10 is isoleucine, amino acid at position 11 is serine, and amino acid at position 12 is phenylalanine)

Head-to-tail cyclized peptide SFTI-8 was synthesized using a synthetic procedure similar to that described in Example 1, except that no disulfide formation reaction was performed in this synthesis since the two cysteine residues were replaced with serine. Direct HPLC purification of the crude SFTI-8 residue afforded by TFA-mediated deprotection yielded SFTI-8 ((RP-HPLC, Retention time=16.0 minutes; gradient 10-80% B over 30 minutes); FAB-MS (M+H)$^+$1484.3 (Calcd.$_{ave}$ 1483.7)).

Example 7

This example describes the synthesis of SFTI-9.

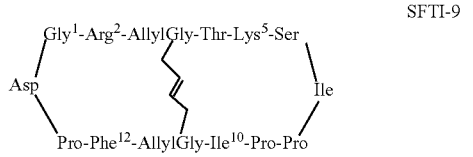

SFTI-9

SFTI-9 (SEQ ID NO: 1, wherein amino acid at position 2 is arginine, amino acid at position 3 is allylglycine, amino acid at position 4 is threonine, amino acid at position 5 is lysine, amino acid at position 10 is isoleucine, amino acid at position 11 is allylglycine, and amino acid at position 12 is phenylalanine)

Head-to-tail cyclized peptide cyclo-(Arg(Pmc)$^2$AllylGly$^3$Thr(Bu$^t$)Lys(Boc)$^5$Ser(Bu$^t$)IleProPro-Ile$^{10}$AllylGly$^{11}$Phe$^{12}$ProAsp(Bu$^t$)Gly$^1$) (SFTI-9) was synthesized using a synthetic procedure similar to that described in Example 1. This purified peptide (20 mg, 0.0098 mmol) was dissolved in anhydrous CH$_2$Cl$_2$ (45 mL), and then the benzylidene-bis(tricyclohexylphosphine)-dichlororuthenium (Grubbs's) catalyst (40 mg, 0.049 mmol) was added. The reaction mixture was gently refluxed under argon atmosphere for 34 hours, cooled and evaporated to dryness in vacuo. To cleave the sidechain protecting groups, the residue was treated with 90% TFA containing 5% each of thioanisole and water for 2 h, followed by removal of TFA in vacuo. The residue was directly purified by RP-HPLC to give the final product (7.5 mg (Yield: 52% from the monocyclic peptide material) ((Retention time=18.0 minutes; gradient 10-80% B over 30 minutes); FAB-MS (M+H)$^+$1476.2 (Calcd.$_{ave}$ 1475.7)).

Example 8

This example describes the synthesis of SFTI-10.

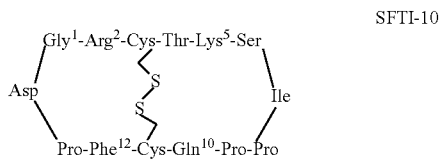

SFTI-10

SFTI-10 (SEQ ID NO: 1, wherein amino acid at position 2 is arginine, amino acid at position 3 is cysteine, amino acid at position 4 is threonine, amino acid at position 5 is lysine, amino acid at position 10 is glutamine, amino acid at position 11 is cysteine, and amino acid at position 12 is phenylalanine)

This bicyclic peptide was prepared using a synthetic procedure similar to that described in Example 1. The crude SFTI-10 residue obtained from TFA-mediated deprotection was purified by HPLC ((RP-HPLC, Retention time=15.1 minutes; gradient 10-80% B over 30 min); FAB-MS (M+H)$^+$ 1530.0 (Calcd.$_{ave}$ 1528.8)).

Example 9

This example describes the purification and characterization of SFTI-11.

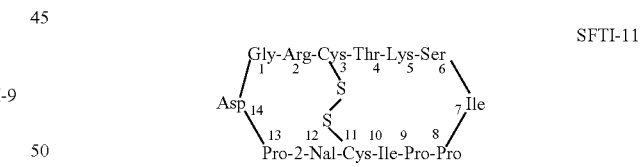

SFTI-11

SFTI-11 (SEQ ID NO: 1, wherein amino acid at position 2 is arginine, amino acid at position 3 is cysteine, amino acid at position 4 is threonine, amino acid at position 5 is lysine, amino acid at position 10 is isoleucine, amino acid at position 11 is cysteine, and amino acid at position 12 is 2-napthylalanine)

With reference to SFTI-11, a 2-napthylalanine (2-Nal) residue is incorporated at the 12 position in place of the phenylalanine found in SFTI-1. The synthesis proceeded by the general method used for the synthesis of SFTI-3 in example 1. Purification of the crude SFTI-11 afforded by TFA mediated deprotection was performed directly by HPLC using HPLC Conditions "II" described above ((Retention time=19.8 minutes); FAB-MS (M+H)$^+$1564.8 (Calcd.$_{ave}$ 1563.8)).

Example 10

This example describes the purification and characterization of SFTI-12.

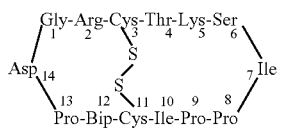

SFTI-12

SFTI-12 (SEQ ID NO: 1) wherein amino acid at position 2 is arginine, amino acid at position 3 is cysteine, amino acid at position 4 is threonine, amino acid at position 5 is lysine, amino acid at position 10 is isoleucine, amino acid at position 11 is cysteine, and amino acid at position 12 is biphenylalanine With reference to SFTI-12, a biphenylalanine (Bip) residue is incorporated at position 12 in place of the phenylalanine found in SFTI-1. The synthesis proceeded by the general method used for the synthesis of SFTI-3 in example 1. Direct HPLC purification of the crude SFTI-12 afforded by TFA mediated deprotection was performed using HPLC Conditions "III" described above ((Retention time=22.0 minutes); FAB-MS $(M+H)^+$ 1591.0 (Calcd.$_{ave}$ 1589.9)).

Example 11

This example describes the purification and characterization of SFTI-13.

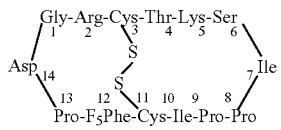

SFTI-13

SFTI-13 (SEQ ID NO: 1; wherein amino acid at position 2 is arginine, amino acid at position 3 is cysteine, amino acid at position 4 is threonine, amino acid at position 5 is lysine, amino acid at position 10 is isoleucine, amino acid at position 11 is cysteine, and amino acid at position 12 is $F_5$phenylalanine)

With reference to SFTI-13, a pentafluorophenylalanine residue ($F_5$Phe) is incorporated at position 12 in place of the phenylalanine found in SFTI-1. The synthesis proceeded by the general method described for the synthesis of SFTI-3 in example 1. Direct HPLC purification of the crude SFTI-13 afforded by TFA mediated deprotection was performed using HPLC Conditions "I" described above ((Retention time=19.4 minutes; FAB-MS $(M+H)^+$ 1604.9 (Calcd.$_{ave}$ 1603.7).

Example 12

This example describes the purification and characterization of SFTI-14.

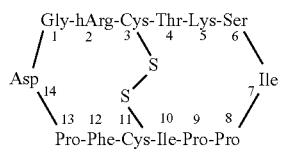

SFTI-14

SFTI-14 (SEQ ID NO: 1, wherein amino acid at position 2 is h-arginine, amino acid at position 3 is cysteine, amino acid at position 4 is threonine, amino acid at position 5 is lysine, amino acid at position 10 is isoleucine, amino acid at position 11 is cysteine, and amino acid at position 12 is phenylalanine)

With reference to SFTI-14, a homoarginine residue (hArg) is incorporated at position 2 in place of the arginine found in SFTI-1. The synthesis proceeded by the general method described for the synthesis of SFTI-3 in example 1. Direct HPLC purification of the crude SFTI-14 afforded by TFA mediated deprotection was performed using HPLC Conditions "I" described above ((Retention time=18.2 minutes); FAB-MS $(M+H)^+$ 1529.0 (Calcd.$_{ave}$ 1527.8)).

Example 13

This example describes the synthesis of SFTI-15.

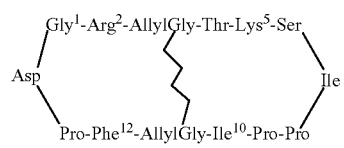

SFTI-15

SFTI-15 (SEQ ID NO: 1, wherein amino acid at position 2 is arginine, amino acid at position 3 is allylglycine, amino acid at position 4 is threonine, amino acid at position 5 is lysine, amino acid at position 10 is isoleucine, amino acid at position 11 is allyglycine, and amino acid at position 12 is phenylalanine)

Bicyclic peptide SFTI-15 was obtained from bicyclic peptide SFTI-9 having an alkenyl linkage described in example 7, by hydrogenation. The olefin-bridged peptide (SFTI-9) (16 mg, 0.011 mmol) was dissolved in $CH_3OH$ (15 mL), and then 10% Pd/C (89 mg) was added. The system was flushed with hydrogen, and the reaction mixture was vigorously stirred at room temperature for 24 h under $H_2$ atmosphere, filtered to remove catalyst and washed the catalyst with $CH_3OH$. The combined filtrate was concentrated to 25 mL, and the solution was filtered with GELMAN 0.45 µm filter (organic solvent stable) to remove fine catalyst. The resulting solution was concentrated to dryness, the residue was dissolved with acetonitrile/water (1:1) and lyophilized to give 14 mg pure product (Yield: 88%). Product characterization: RP-HPLC, (Retention time=20.7 minutes; Vydac C8 colunm (22×250 mm); gradient, 10%-80% B over 30 minutes; flow rate, 10.0 mL/minute; UV detector 225 nm); FAB-MS $(M+H)^+$ 1478.1 (Calcd.$_{iso}$ 1476.8).

---

We claim:

1. A compound or salt thereof, comprising the formula

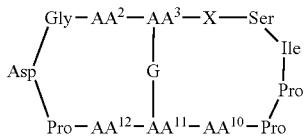

(SEQ ID NO:1)

wherein $AA^2$, $AA^3$, $AA^{10}$, $AA^{11}$ and $AA^{12}$ are amino acids; $AA^3$-G-$AA^{11}$ selected from

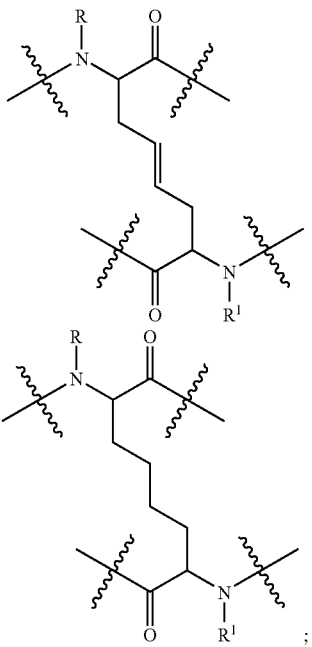

R and $R^1$ independently are selected from H and lower alkyl; and

X is the dipeptide Thr-$AA^5$, wherein $AA^5$ is an amino acid.

2. The compound according to claim 1, wherein $AA^5$ is a basic amino acid.

3. The compound according to claim 2, wherein $AA^5$ is a lysine.

4. The compound according to claim 1, wherein $AA^2$ is a basic amino acid.

5. The compound according to claim 4, wherein $AA^2$ is an arginine.

6. The compound according to claim 1, wherein $AA^{10}$ is a hydrophobic amino acid.

7. The compound according to claim 1, wherein $AA^{12}$ is an aromatic amino acid.

8. The compound according to claim 1, wherein the compound is a serine protease inhibitor.

9. A pharmaceutical composition comprising an amount of a compound according to claim 1, effective to inhibit or decrease serine protease activity in a subject and a pharmaceutical carrier.

10. The pharmaceutical composition according to claim 9, wherein the composition comprises plural different compounds.

11. The composition according to claim 9, wherein $AA^2$ represents a cationic amino acid $AA^{10}$ represents a hydrophobic amino acid $AA^{12}$ represents an aromatic amino acid; and $AA^5$ comprises a cationic group.

12. The composition according to claim 9, wherein $AA^2$ represents arginine, guanidinophenylalanine or homoarginine; $AA^{10}$ represents glycine, proline or phenylalanine; $AA^{12}$ represents biphenylalanine, 2-napthylalanine, pentafluorophenylalanine or phenylalanine.

13. The composition according to claim 9, wherein $AA^5$ is selected from the group consisting of alanine, glycine, serine, threonine, lysine, homolysine, ornithine, arginine, aminoserine, aminopiperidinecarboxylic acid, pyrrolidinylalanine and histidine.

14. The composition according to claim 9, wherein $AA^2$ represents arginine, guanidinophenylalanine or homoarginine; $AA^{10}$ represents glycine, proline or phenylalanine; $AA^{12}$ represents biphenylalanine, 2-napthylalanine, pentafluorophenylalanine or phenylalanine; and $AA^5$ is selected from the group consisting of alanine, glycine, serine, threonine, lysine, homolysine, ornithine, arginine, aminoserine, aminopiperidinecarboxylic acid, pyrrolidinylalanine and histidine.

15. The pharmaceutical composition according to claim 9, wherein the composition is effective to inhibit or decrease the serine protease activity of matriptase or MTSP1.

16. The pharmaceutical composition according to claim 9, wherein the compound has a $K_i$ of less than about 1 micromolar for matriptase, MTSP1, or both.

17. The pharmaceutical composition according to claim 9, wherein the compound has a $K_i$ of less than about 500 nanomolar for matriptase, MTSP1, or both.

18. The pharmaceutical composition according to claim 9, wherein the compound has a $K_i$ of less than about 50 nanomolar for matriptase, MTSP1, or both.

19. A compound, having the formula

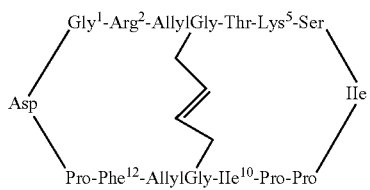

SFTI-9 (SEQ ID NO: 1, wherein amino acid at position 2 is arginine, amino acid at position 3 is allyglycine, amino acid at position 4 is threonine, amino acid at position 5 is lysine, amino acid at position 10 is isoleucine, amino acid at position 11 is allyglycine, and amino acid at position 12 is phenylalanine) or

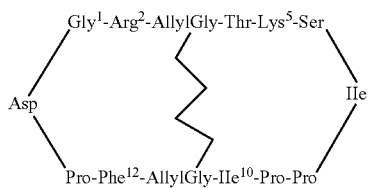

SFTI-15 (SEQ ID NO: 1, wherein amino acid at position 2 is arginine, amino acid at position 3 is allyglycine, amino acid at position 4 is threonine, amino acid at position 5 is lysine, amino acid at position 10 is isoleucine, amino acid at position 11 is allyglycine, and amino acid at position 12 is phenylalanine).

20. The compound according to claim 19 having the formula

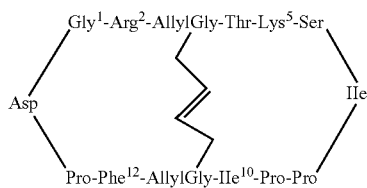

SFTI-9 (SEQ ID NO: 1, wherein amino acid at position 2 is arginine, amino acid at position 3 is allyglycine, amino acid at position 4 is threonine, amino acid at position 5 is lysine, amino acid at position 10 is isoleucine, amino acid at position 11 is allyglycine, and amino acid at position 12 is phenylalanine).

* * * * *

UNITED STATES PATENT AND TRADEMARK OFFICE
CERTIFICATE OF CORRECTION

PATENT NO.        : 7,439,226 B2
APPLICATION NO. : 10/957266
DATED              : October 21, 2008
INVENTOR(S)       : Roller et al.

It is certified that error appears in the above-identified patent and that said Letters Patent is hereby corrected as shown below:

Column 1, Line 66, "STFI-1" should be --SFTI-1--.

Column 3, Line 11, "cancer) ocular" should be --cancer), ocular--.

Column 3, Line 58, "$AA^5 \ AA^{10}$" should be --$AA^5, AA^{10}$--.

Column 4, Line 56, "alkoxy" should be --alkoxy.--.

Column 5, Line 26, "napthylalanine" should be --naphthylalanine--.

Column 5, Line 49, "2-napthylalanine" should be --2-naphthylalanine--.

Column 7, Line 29, "thereof," should be --thereof;--.

Column 8, Lines 20-21, "acid-threonine threonine-pyrrolidinylalanine," should be --acid-threonine, threonine-pyrrolidinylalanine,--.

Column 8, Line 22, "histidine-threonine equivalent dipeptides thereof" should be --histidine-threonine, equivalent dipeptides thereof--.

Column 8, Lines 27-28, "alanine-amino serine," should be --alanine-aminoserine,--.

Column 9, Line 20, "according Formula 2" should be --according to Formula 2--.

Column 9, Lines 29-30, "pyrrolidinyl alanine" should be --pyrrolidinylalanine--.

Column 9, Line 48, "Formula 3 X" should be --Formula 3, X--.

Column 12, Line 55 (in Table 1), "[Ki" should be --[$K_i$--.

Column 13, Line 11 (in Table 1-continued), "[Ki" should be --[$K_i$--.

Column 15, Line 26, "topical parenteral," should be --topical, parenteral,--.

Column 17, Lines 60-61, "(tricyclohexylphosphine-dichlororuthenium" should be --(tricyclohexylphosphine-dichlororuthenium)--.

UNITED STATES PATENT AND TRADEMARK OFFICE
CERTIFICATE OF CORRECTION

PATENT NO. : 7,439,226 B2
APPLICATION NO. : 10/957266
DATED : October 21, 2008
INVENTOR(S) : Roller et al.

It is certified that error appears in the above-identified patent and that said Letters Patent is hereby corrected as shown below:

Column 18, Line 37, "N-t-Boc Leu-Arg-Arg-AMC" should be
--N-t-Boc-Leu-Arg-Arg-AMC--

Column 19, Line 2, "$AA^{10}$ isoleucine," should be --$AA^{10}$ is isoleucine,--.

Column 19, Line 24, "DEEA" should be --DIEA--.

Column 22, Lines 8-9, "(7.5 mg (Yield:" should be --(7.5 mg) (Yield:--.

Column 22, Lines 57-58, "2-napthylalanine" should be --2-naphthylalanine--.

Column 22, Line 60, "2-napthylalanine" should be --2-naphthylalanine--.

Column 23, Line 50, "minutes;...1603.7)" should be --minutes);...1603.7))--.

Column 24, Line 36, "allyglycine" should be --allylglycine--.

Column 24, Line 52, "Colunm" should be --Column--.

Column 25, Line 29 (in claim 1), "$AA^3$-G-$AA^{11}$ selected from" should be
--$AA^3$-G-$AA^{11}$ is selected from--.

Column 26, Lines 32-33 (in claim 11), "acid $AA^{10}$...acid $AA^{12}$" should be --acid; $AA^{10}$...acid; $AA^{12}$--.

Column 26, Line 39 (in claim 12), "2-napthylalanine" should be --2-naphthylalanine--.

Column 26, Line 49 (in claim 14), "2-napthylalanine" should be --2-naphthylalanine--.

Column 27, Line 13 (in claim 19), "allyglycine" should be --allylglycine--.

Column 27, Line 16 (in claim 19), "allyglycine" should be --allylglycine--.

Column 28, Line 2 (in claim 19), "allyglycine" should be --allylglycine--.

Column 28, Line 5 (in claim 19), "allyglycine" should be --allylglycine--.

Column 28, Line 21 (in claim 20), "allyglycine" should be --allylglycine--.

UNITED STATES PATENT AND TRADEMARK OFFICE
CERTIFICATE OF CORRECTION

PATENT NO. : 7,439,226 B2
APPLICATION NO. : 10/957266
DATED : October 21, 2008
INVENTOR(S) : Roller et al.

It is certified that error appears in the above-identified patent and that said Letters Patent is hereby corrected as shown below:

Column 28, Line 24 (in claim 20), "allyglycine" should be --allylglycine--.

Signed and Sealed this

Twentieth Day of October, 2009

David J. Kappos
*Director of the United States Patent and Trademark Office*

SEQUENCE LISTING

<160> NUMBER OF SEQ ID NOS: 1

<210> SEQ ID NO 1
<211> LENGTH: 14
<212> TYPE: PRT
<213> ORGANISM: Artificial Sequence

```
-continued
<220> FEATURE:
<223> OTHER INFORMATION: Synthetic peptide
<220> FEATURE:
<221> NAME/KEY: misc_feature
<222> LOCATION: (2)..(5)
<223> OTHER INFORMATION: Xaa can be any amino acid
<220> FEATURE:
<221> NAME/KEY: misc_feature
<222> LOCATION: (10)..(12)
<223> OTHER INFORMATION: Xaa can be any amino acid

<400> SEQUENCE: 1

Gly Xaa Xaa Xaa Xaa Ser Ile Pro Pro Xaa Xaa Xaa Pro Asp
1               5                   10
```